United States Patent [19]

Rytz et al.

[11] Patent Number: 4,942,238
[45] Date of Patent: Jul. 17, 1990

[54] UNSATURATED DERIVATIVES OF 2,2,6,6-TETRAMETHYLPIPERIDINE

[75] Inventors: Gerhard Rytz, Schwarzenburg; Mario Slongo, Tafers, both of Switzerland

[73] Assignee: Ciba-Geigy Corporation, Ardsley, N.Y.

[21] Appl. No.: 355,218

[22] Filed: May 22, 1989

[30] Foreign Application Priority Data

May 27, 1988 [CH] Switzerland .................. 2007/88

[51] Int. Cl.$^5$ .......................................... C07D 239/00
[52] U.S. Cl. .................................................. 546/242
[58] Field of Search ........................................ 546/242

[56] References Cited

U.S. PATENT DOCUMENTS

| 3,705,166 | 12/1972 | Murayama et al. | 546/244 |
| 4,014,887 | 3/1977 | Randell et al. | |
| 4,046,737 | 9/1977 | Holt et al. | |
| 4,731,393 | 3/1988 | Karrer et al. | 524/102 |
| 4,731,448 | 3/1988 | Issler et al. | 546/242 |

OTHER PUBLICATIONS

Slongo et al: Light Stabilized, Starshaped Microparticles C.A. 111: 25003b (1989).

Primary Examiner—Joseph L. Schofer
Assistant Examiner—Alex H. Walker
Attorney, Agent, or Firm—Luther A. R. Hall

[57] ABSTRACT

Compounds of formula I

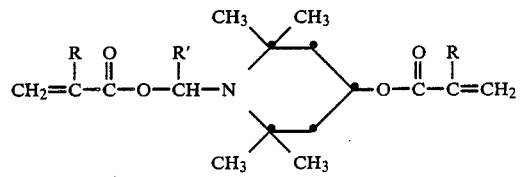

wherein R is hydrogen, methyl or cyano, and R' is hydrogen, $C_1$–$C_8$alkyl or phenyl, are suitable for copolymerization with ethylenically unsaturated monomers to form crosslinked copolymers which are stabilized against light.

4 Claims, No Drawings

UNSATURATED DERIVATIVES OF 2,2,6,6-TETRAMETHYLPIPERIDINE

The present invention relates to novel compounds which are unsaturated derivatives of 2,2,6,6-tetramethylpiperidine, and to the use thereof as light stabilisers and crosslinking agents.

Specifically, the invention relates to compounds of formula I

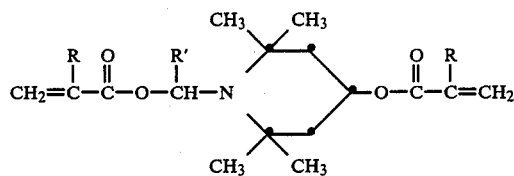

wherein R is hydrogen, methyl or cyano, and R' is hydrogen, $C_1$–$C_8$ alkyl or phenyl.

It is known that derivatives of tetramethylpiperidine can be used as light stabilisers, especially in polymers. Tetramethylpiperidine derivatives which are substituted in 1- and 4-position are disclosed in German Offenlegungsschrift No. 2 258 752.

German Offenlegungsschrift No. 2 040 983 also discloses acrylic acid derivatives of 2,2,6,6-tetramethyl-4-piperidinol which can be incorporated into polymers by copolymerisation. European patent application No. 101 411 discloses s-triazine derivatives which, in addition to tetramethylpiperidine groups, contain several ethylenically unsaturated groups, and which are suitable for crosslinking polyolefins.

The compounds of formula I are suitable for the preparation of crosslinked polymers by copolymerisation with ethylenically unsaturated monomers.

Preferred compounds of formula I are those wherein R and R' are each independently of the other hydrogen or methyl.

Examples of compounds of formula I are:
1-(2-acryloyloxyethyl)-4-acryloyloxy-2,2,6,6-tetramethylpiperidine,
1-(2-methacryloyloxyethyl)-4-methacryloyloxy-2,2,6,6-tetramethylpiperidine,
1-[2-(α-cyanoacryloyloxy)ethyl]-4-(α-cyanoacryloyloxy)-2,2,6,6-tetramethylpiperidine,
1-(2-acryloyloxypropyl)-4-acryloyloxy-2,2,6,6-tetramethylpiperidine,
1-(2-methacryloyloxybutyl)-4-methacryloyloxy-2,2,6,6-tetramethylpiperidine,
1-(2-acryloyloxy-2-phenylethyl)-4-acryloyloxy-2,2,6,6-tetramethylpiperidine.

The compounds of formula I may be prepared from the diols of formula II

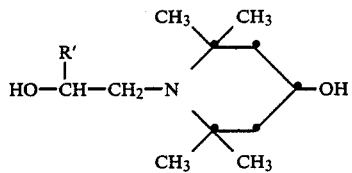

by acylation of both OH groups with the acids of formula $CH_2$=C(R)—COOH or their esters or acid chlorides by methods which are known per se. It is preferred to use the esters of lower alcohols of formula $CH_2$=C(R)—COO—($C_1$-$C_4$ alkyl), with the concurrent use of a transesterification catalyst. Examples of suitable transesterification catalysts are tetraalkyl titanates, alkali metal alkoxides or alkali metal amides. To prevent polymerisation during the synthesis, small amounts of a polymerisation inhibitor will preferably be added. Isolation and purification of the products can be effected by conventional methods, for example by crystallisation, high vacuum distillation or chromatography. The compounds of formula II are known compounds and are disclosed, for example, in German Offenlegungsschrift No. 2 352 658.

An alternative method of preparing the compounds of formula I comprises esterifying a diol of formula II with a β-halocarboxylic acid and subsequently dehydrohalogenating the ester by reaction with a base.

The compounds of formula I may be used as light stabilisers for organic polymers. Examples of such polymers are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene-propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in (1) above, for example polypropylene/ethylene-propylenecopolymers, LDPE/EVA, LDPE/EAA, LLDPE/EVA and LLDPE/EAA copolymers.

3a. Hydrocarbon resins (for example $C_5$–$C_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/ butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile copolymers; styrene and acrylonitrile (or methacrylonitrile) on polybutadiene; styrene and maleimide on polybutadiene; styrene, acrylonitrile and maleic anhydride or maleimide on polybutadiene; styrene, acrylonitrile and methyl methacrylate on polybutadiene, styrene and alkylacrylates or alkylmethacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for example the copolymer mixtures known as ABS, MBS, ASA or AES polymers.

7. Halogenated polymers such as polychloroprene, chlorinated rubber, chlorinated or sulfochlorinated polyethylene, epichlorohydrin homo- and copolymers, polymers of halogenated vinyl compounds, for example polyvinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under (8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in (1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and aliphatic or aromatic polyisocyanates on the other, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic and/or terephthalic acid and optionally an elastomer as modifier, for example poly-2,4,4,-trimethylhexamethylene terephthalamide or poly-m-phenylene isophthalamide, block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Crosslinkable acrylic resins derived from substituted acrylic esters, such as epoxy acrylates, urethane acrylates or polyester acrylates.

24. Alkyd resins, polyester resins or acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; resins and their derivatives.

27. Mixtures (polyblends) of the aforementioned polymers, for example PP/EPDM, polyamide/EPDM or ABS, PVC/EVA, PVC/ABS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 66 and copolymers, PA/HDPE, PA/PP, PA/PPO.

The compounds of formula I are preferably added in an amount of 0.01 to 5% by weight, most preferably 0.05 to 2% by weight, based on the polymer to be stabilised. The addition can be made by mixing the compounds of formula I with the polymer in any stage of processing. In addition to the compound of formula I, still further stabilisers or other modifiers can be added, for example the following additives:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n- butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis-(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-triazine, and octyl N-(3,5-di-tert-butyl-4-hydroxyphenyl)carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-secbutyl-5'-tert-butyl, 4'-octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methylphenyl undecyl ketonoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butane tetracarboxylate, 1,1'-(1,2-ethanediyl)bis-(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides and mixtures of o- and p-ethoxy-disubstituted oxanilides.

3. Metal passivators, for example N,N'-diphenyloxalodiamide, N-salicylal-N'-salicyloylhydrazine, N,N'- bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-ditertbutylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of $\beta$-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis($\beta$-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or tin pyrocatecholate.

8. Nucleating agents, for example 4-tert-butylbenzoic acid, adipic acid, diphenylacetic acid.

9. Fillers and reinforcing agents, for example calcium carbonate, silicates, glass fibres, asbestos, talcum, kaolin, mica, barium sulfate, metal oxides and hydroxides, carbon black, graphite.

10. Other additives, for example plasticisers, lubricants, emulsifiers, pigments, fluorescent whitening agents, flame retardants, antistatic agents, blowing agents.

The compounds of formula I are preferably used for copolymerisation with other ethylenically unsaturated monomers to form crosslinked copolymers. Examples of such copolymerisable monomers are derivatives of acrylic acid, methacrylic acid, crotonic acid or maleic acid (especially their esters, amides and nitriles), vinyl esters of aliphatic carboxylic acids, vinyl chloride, vinylidene dichloride, styrene, $\alpha$-methylstyrene or N-vinylpyrrolidone.

The copolymers may also contain two or more such unsaturated monomers. They may also contain monomers having two or more ethylenic double bonds which act as crosslinking agents. Examples of such crosslinking agents are, in particular, polyol poly(meth)acrylates such as ethylene glycol diacrylate, butanediol dimethacrylate or pentaerythritol tetraacrylate.

The invention thus also relates to crosslinked copolymers obtainable from (a) at least one ethylenically unsaturated monomer and (b) a compound of formula I. The compound of formula I is preferably present in the copolymer in an amount of 0.5 to 10% by weight.

When this copolymerisation is carried out under dispersing conditions in an inert solvent in which the copolymer is insoluble, a polymer dispersion consisting of crosslinked microparticles is obtained. These microparticles can be used for producing paints of high solids content as described, for example, in European patent application 003 166.

The concurrent use of compounds of formula I as comonomers in the preparation of such polymer microparticles has two advantages. First, the bifunctional piperidine compound acts as crosslinking agent. Second, the microparticles are thereby stabilised against light, especially against UV light, so that paints containing such microparticles are also stabilised. The paints contain the microparticles as disperse phase dispersed in a liquid phase consisting of binder and solvent. Because it is chemically bonded in the microparticles, the light stabiliser cannot evaporate when such paints are heat cured. Even when using such paints, the light stabiliser cannot be lost through elution or migration.

It is, however, not only possible to use the compounds of formula I as microparticles for paints of high solids content, but also for other utilities for which a crosslinked polymer required.

The following Examples illustrate the preparation of the compounds of this invention and the use thereof. Parts and percentages are by weight, unless otherwise indicated.

EXAMPLE 1

1-(2-Methacryloyloxyethyl)-4-methacryloyloxy-2,2,6,6-tetramethylpiperidine

A mixture of 201.3 g of 1-(2-hydroxyethyl)-4-hydroxy-2,2,6,6-tetramethylpiperidine, 360.4 g of methyl methacrylate, 1.5 g of 2,6-di-tert-butyl-p-cresol and 0.4 g of N,N'-bis[$\beta$-(3,5-di-tert-butyl-4-hydroxyphenyl)propionyl]hexamethylenediamine are heated, under nitrogen, at 110° C. until 20 ml of methyl methacrylate have distilled through a Vigreux column (40 cm effective length, with double jacket, metal-coated and evacuated). After cooling to 85° C., 2.4 ml of tetrabutyl titanate are added and the mixture is heated such that methanol distills very slowly (bath temperature 110° C., still temperature 60° C.). After 2 hours, 80.1 g of methyl methacrylate are added and the reaction is allowed to continue for a further 14 hours. Then 1.2 ml of tetrabutyl titanate are added and the reaction is allowed to continue for a further 24 hours under the same conditions. Excess methyl methacrylate is removed by distillation. The residual crude product is purified by chromatography through a column of $SiO_2$ (eluant: 9:1 mixture of ether/methanol (saturated with $NH_3$)), to give pure 1-(2-methacryloyloxyethyl)-4-methacryloyloxy-2,2,6,6-tetramethylpiperidine in the form of a colourless oil; $n_D^{20}=1.485$.

Analysis: calculated: C=67.63% H=9.26% N=4.15%; found: C=67.61% H=9.22% N=4.04%.

EXAMPLE 2

1-(2-Acryloyloxyethyl)-4-acryloyloxy-2,2,6,6-tetramethylpiperidine

The procedure of Example 1 is repeated, using butyl acrylate instead of methyl methacrylate, to give 1-(2-acryloyloxyethyl)-4-acryloyloxy-2,2,6,6-tetramethylpiperidine as a colourless oil.

Analysis: calculated: C=66.0% H=8.8% N=4.5%; found: C=67.7% H=9.0% N=4.6%.

EXAMPLE 3

1-(2-Acryloyloxypropyl)-4-acryloyloxy-2,2,6,6-tetramethylpiperidine

With stirring and cooling with an ice bath, 91.4 g of 3-chloropropionyl chloride, mixed with 60 ml of toluene, are added dropwise to 64.6 g of 1-(2-hydroxypropyl)-4-hydroxy-2,2,6,6-tetramethylpiperidine, 181.8 g of triethylamine and 300 ml of toluene such that the temperature does not exceed 60° C. The reaction mixture is then heated for 3.5 hours to 60° C. After addition of 9.1 g of 3-chloropropionyl chloride, stirring is continued for 1 hour at 60° C. The reaction mixture is then cooled, filtered, and the liquid phase is washed with 4×150 ml of water, dried and concentrated by evaporation. The residue is dissolved in hexane/acetone and the solution is purified by chromatography through a column of SiO$_2$, to give pure 1-(2-acryloyloxypropyl)-4-acryloyloxy-2,2,6,6-tetramethylpiperidine as a slightly yellowish oil of n$_D^{20}$=1.486 (nitrogen content: calculated: 4.33%, found: 4.17%).

EXAMPLE 4

1-(2-Methacryloyloxypropyl)-4-methacryloyloxy-2,2,6,6-tetramethylpiperidine

The procedure of Example 1 is repeated, replacing 1-(2-hydroxyethyl)-4-hydroxy-2,2,6,6-tetramethylpiperidine by 1-(2-hydroxypropyl)-4-hydroxy-2,2,6,6-tetramethylpiperidine, and using toluene as solvent at the conclusion and purifying the crude product by chromatography through a column of SiO$_2$, to give pure 1-(2-methacryloyloxypropyl)-4-methacryloyloxy-2,2,6,6-tetramethylpiperidine as a slightly yellowish oil of n$_D^{20}$=1.482 (nitrogen content: calculated: 3.99%, found: 3.88%).

What is claimed is:

1. A compound of formula I

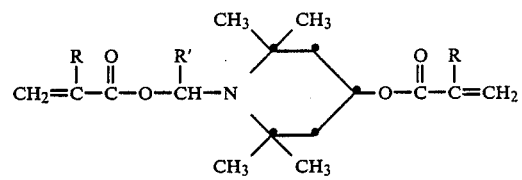

wherein R is hydrogen, methyl or cyano, and R' is hydrogen, C$_1$–C$_8$alkyl or phenyl.

2. A compound according to claim 1 of formula I, wherein R and R' are each independently of the other hydrogen or methyl.

3. 1-(2-Acryloyloxyethyl)-4-acryloyloxy-2,2,6,6-tetramethylpiperidine according to claim 1.

4. 1-(2-Methacryloyloxyethyl)-4-methacryloyloxy-2,2,6,6-tetramethylpiperidine according to claim 1.

* * * * *